United States Patent [19]

Cortina

[11] Patent Number: 4,790,840
[45] Date of Patent: Dec. 13, 1988

[54] COMBINED DISPOSABLE DIAPER AND CLEANING WIPE

[76] Inventor: Cathy Cortina, 3470 Foxcroft Rd., Miramar, Fla. 33024

[21] Appl. No.: 109,672

[22] Filed: Oct. 19, 1987

[51] Int. Cl.[4] ............................................. A61F 13/16
[52] U.S. Cl. ................................................. 604/385.1
[58] Field of Search ..................... 604/385.1, 386, 396

[56] References Cited

U.S. PATENT DOCUMENTS 3,369,545 2/1968 Wanberg ........................... 604/385.1
4,221,221 9/1980 Ehrlich ................................ 604/386

Primary Examiner—John D. Yasko
Attorney, Agent, or Firm—John Cyril Malloy

[57] ABSTRACT

The combination of a wiper element contained in a closed package assembly which is mounted or connected to a diaper assembly, preferably of the disposable diaper type, so as to provide an efficient cleaning facility for cleaning deposited solid and liquid waste from the skin of an infant wherein such waste comes into direct contact with the infant's skin necessitating removal thereof when the diaper is changed.

11 Claims, 1 Drawing Sheet

COMBINED DISPOSABLE DIAPER AND CLEANING WIPE

BACKGROUND OF THE INVENTION

1. Field of the Invention

A cleaning element used in combination with a disposable diaper assembly to facilitate the cleaning of waste material from the skin of an infant after removal of the diaper assembly and disposal thereof.

2. Description of the Prior Art

It is common practice to use some type of diaper structure in children ranging in age from newborn infants to at least one year or until such infant is properly toilet trained. One common problem associated with the use of diapers is the inconvenience of properly cleaning the waste material, both liquid and solid, from the infants buttocks and genitalia area after the infant deposits such waste material within the diaper. While, for the most part, the majority of such waste material is removed from the infant and disposed of along with the diaper, there still remains a significant amount exposed directly to the skin of the infant which would cause discomfort, irritation, odor and a number of other undesirable features if such waste material were in fact not thoroughly and completely removed from the skin of the infant.

Typically, the material from which the diaper is formed does not adequately lend itself to accomplish such cleaning to the extent necessary. Cloth diapers are usually absorbent to the extent that almost the entire diaper becomes "soaked" with liquid waste, thereby rendering it unsanitary to utilize in the performance of such cleaning techniques. On the other hand, a more modern disposable diaper includes an absorbent material generally only along the interior portions thereof wherein the exterior material or covering of the disposable diaper is generally non-absorbent and thereby clearly inapplicable for the use in thoroughly cleaning the waste material from the infant.

Therefore, the person caring for the infant and removing the diaper after becoming soiled, must almost always utilize an additional cleaning facility such as a cloth, sponge, etc. which preferably must first be subjected to exposure to a cleaning composition, sanitizing agent or the like. Therefore, it is readily apparent that in the prior art use, even with the more convenient disposable diapers, of supplementary cleaning facilities is necessary in order to ensure that the infant is properly cleaned and "sanitized" through the removal of all waste material not absorbed by or carried with the diaper upon removal from the infant and/or disposal thereof.

Attempts to correct the problems of the type set forth above are evident in the structure and process disclosed in the Norris U.S. Pat. No. 4,417,894. As disclosed therein, Norris is directed to an improved disposable diaper containing a towelsheet superimposed on or above the back sheet of a diaper and which may be unfastened from its normal position and used as a cleaning element to remove solid waste from the child during the diaper removal process. While applicable for its intended function, the use of a towelsheet directly in the structure of the disposable diaper would appear to necessitate a structural modification of the disposable diaper itself rather than being readily adaptable for use with disposable diaper structures which are presently commercially available. Other structures generally relating to the subject of pre-packaged cleaning utensils, moistened wipes, etc. are disclosed in the Herwood U.S. Pat. No. 4,332,319, and Stuart, Jr., U.S. Pat. No. 3,561,456.

SUMMARY OF THE INVENTION

The present invention is directed towards a combination of a cleaning assembly or utensil preferably in the form of a moistened wiping cloth, and a diaper of the type worn by children ranging in age from newborn infants until such infant is toilet trained. More specifically, the aforementioned wipe is pre-packaged by means of a package mounted preferably on an exterior surface of the diaper structure in an accessible location for a mother or other adult who is removing the diaper from the children after use. As set forth above, the cleaning wipe is pre-saturated with a liquid which is preferably a cleaning composition. The cleaning composition is formulated from a plurality of ingredients specifically designed to be non-irritating in terms of coming in direct contact with the delicate skin of an infant or young child. It is also formulated specifically to clean, sanitize and remove either solid or liquid waste from the buttocks, genitalia and overall skin area of the infant.

Therefore, the package means of the present invention should be made of a material which is resistant to liquid passing therethrough. This ensures that the liquid composition carried by the cleaning wipe will not evaporate due to excessive exposure to atmosphere. To the contrary, the cleaning composition will be maintained or carried by the cleaning wipe so as to facilitate and render more efficient the cleaning and sanitation procedure necessary to remove all waste from direct contact from the skin of the infant after depositing of such waste by the infant into the diaper.

The package means includes a closure means thereon which is specifically structured to prevent ready access to the hollow interior of the package by the infant wearing the diaper. However, such closure means should not be structured to be resistant to opening to the extent of rendering access to the pre-packaged cleaning wipe inconvenient by an adult user thereof.

While in a preferred embodiment, to be described in greater detail hereinafter, the package is fixedly secured to an exterior surface of the diaper, the present invention also contemplates positioning of the package in any other accessible position which is non-irritating to the infant wearing the diaper. Also, it is further contemplated that in certain embodiments the package containing the wipe may be removable from its mounted position prior to or after opening of the package by removal of the closure means.

In such an embodiment it should again be emphasized that placement of the package is particularly important in terms of rendering it at least partially inaccessible to the infant wearing the diaper.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature of the present invention, reference should be had to the following detailed description taken in connection with the accompanying drawing in which.

Like reference numerals refer to like parts throughout the several views of the drawings.

DETAILED DESCRIPTION OF THE PREFERRED EMBODIMENT

Figure 1:
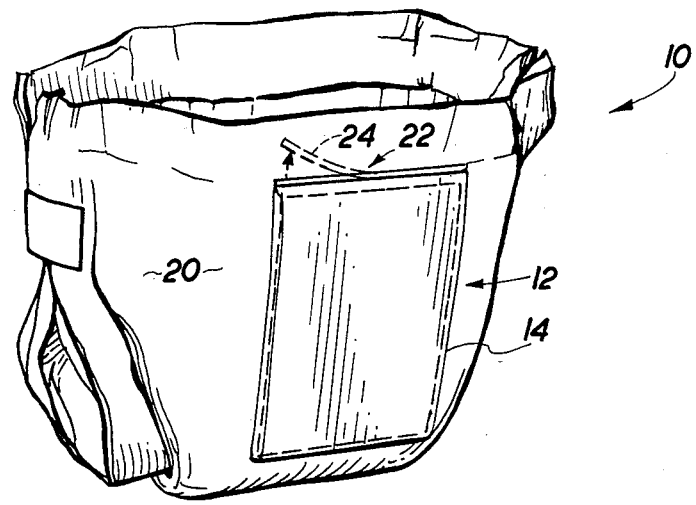
FIG. 1 is perspective view of the diaper with a pre-packaged cleaning assembly secured on an outer surface thereof, and further, wherein a closure portion associated with the package is represented in phantom lines in a partially removed position.
Figure 2:
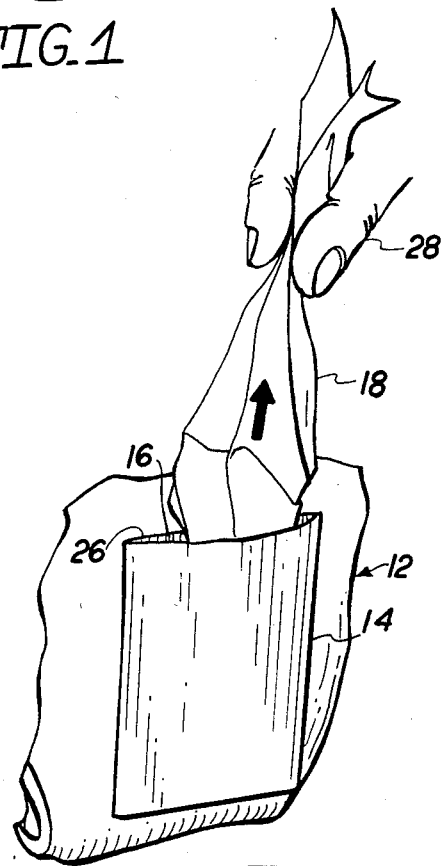
FIG. 2 is a perspective view in partial cut-away showing removal of a cleaning wipe from the interior of the package after removal of the closure therefrom.

As shown in FIGS. 1 and 2, the present invention is directed to the combination of a diaper assembly generally indicated as 10 and preferably being a disposable diaper, and a cleaning assembly generally indicated as 12. As shown both in FIGS. 1 and 2, the cleaning assembly comprises a package means 14 formed of a material which is preferably resistant to the passage of liquid therethrough and is thereby "liquid-proof." The package 14 contains a hollow interior 16 of sufficient dimension and configuration to contain a wiping utensil or element 18 therein. The wiping element 18 is formed of a natural or synthetic material, cloth, etc. specifically structured to have a sufficient dimension to provide enough surface area and "body" of the wipe element 18 to allow a thorough cleaning of the buttocks, genitalia and skin area which may come into contact with either solid or liquid waste products. Since it normally the case that the diaper structure is not immediately removed from the infant after depositing of waste therein, such waste usually comes into contact with the skin of the infant, sometimes for a relatively prolonged period. The waste material, specifically solid waste, is frequently difficult to remove since the diaper structure 10 is already soiled and contains a non-absorbent outer cover 20 which does not lend itself to the absorbent removal of waste products from the skin of the infant as set forth above. Accordingly, in actual practice, it is common for a mother or other adult in charge of the infant's care, to maintain a separate supply of cleaning elements of cloths which also may necessitate the use of some type of liquid cleansing composition or sanitizing composition. This, of course, is an inconvenient manner of adequately cleaning the infant since such supplementary products are not always available at the time or location where the disposable diaper 10 is removed from the infant and a new diaper structure replaced thereon.

Naturally, it is of extreme importance for the healthy care of the infant to clean all such waste material, including urine and fecal matter from the skin contacted thereby. Prolonged exposure to such waste material will result in irritation, rash, and almost certain discomfort of the infant.

Therefore, the cleaning wipe 18 is further impregnated or caused to at least partially absorb and thereby maintain a moistened state through the application thereto of a cleaning composition. Such cleaning composition may be formed of conventional cleaning ingredients which are specifically determined not to be irritating to tender skin, especially of a newborn infant. It is also further important that the material from which the package 14 is formed is "liquid-proof" so as to maintain the wipe 18 in a moistened state through the prevention of evaporation of the cleaning composition from the cleaning wipe 18 or the interior of the package means 14 by prolonged exposure to atmosphere.

The package means 14 does include a closure means generally indicated as 22 having a tear strip 24 secured over an opening 26 and disposed in covering relation thereto when in its closed position as represented in solid lines in FIG. 1. However, the tear strip 24 may be secured in its covering relation to the opening 26 by means of a weakened segment line which facilitates the tearing away of the tear strip 24 when removed therefrom as indicated in phantom lines in FIG. 1. Since the opening 26 is contiguous to the hollow interior portion 16 of the package means 14 in which the wipe element 18 is disposed, clear access is provided to the wipe 18 by the fingers 28 of a user thereof.

As shown in FIG. 1, the package means 14 is preferably fixedly secured to an outer surface of the diaper structure 10 so as not to be readily removed therefrom inadvertently by the infant. Further, the closure means 22 is secured in its covering and closing relation to the opening 26 with sufficient security so as to prevent or make difficult the inadvertent or "unauthorized" opening of the package means 14 by the infant. The closure means 22 should therefore be structured to be substantially "child-proof."

In another embodiment of the present invention, the package means 14 can in fact be removable from a mounted position on the diaper structure 10 either prior to or after removal of the tear strip 24 from its covering relation to the opening 26 of the package means 14. This is to add to the convenience of the user of the wipe 18 such as when the wipe is desired to be used for a general cleaning of the infant rather than specifically cleaning the waste material from the infant's skin after depositing of such on the interior of the diaper. For example, the package 14 can be removed, opened and the wipe 18 can be removed from the interior 16 so as to be used to clean the infant's face or other portions of his body. The entire package and wipe can then be disposed of independently of the diaper structure 10. In this embodiment the removal of package assembly 14 should be sufficiently difficult to prevent such removal by the infant such as with the use of a relatively "strong" but releasable adhesive disposed to secure the package to the diaper's outer surface.

Alternately, to the above-described embodiment, the closure means 22 can have a recloseable or reusable structure, conventional in the art and commonly known as a "zip-lock" closure element operable after an initial tear strip 24 has been removed. This would enable storing of the wipe 18 for reuse or a sanitary disposal thereof after the wipe 18 is returned to the package means 14.

Now that the invention has been described, what is claimed is:

1. A cleaning assembly for use in combination with a disposable diaper structure, said assembly comprising:
   a. a wiper element formed of a liquid absorbent material and having sufficient softness in texture to be applied to the skin of an infant,
   b. a cleaning composition applied to said wiper element and carried thereby, and being of sufficient quantity to moisten said wiper element,
   c. a package means secured to the diaper structure having a hollow interior for the containment of the wiper element therein, d. said package means having an opening formed thereon in contiguous relation to aid hollow interior and defining an access to and from said hollow interior of said package means, e. closure means mounted on said package means adjacent said opening for selectively positioning said opening between an open and closed position, f. said package means formed of a liquid-proof material and dimensioned and configured to contain said wiper element and moisture therein within said hollow interior, g. whereby said wiper element is readily available for cleaning of an infant's skin on which the diaper structure is mounted, and h. said closure means comprising a tear strip integrally formed on said package means in covering, closing relation to said opening, said tear strip secured to the remainder of said package by a weakened segment line extending along the length of said tear strip and serving to removably interconnect said tear strip to the remainder of said package means.

2. An assembly as in claim 1 wherein said package means is fixedly secured to an outer surface of the diaper structure.

3. An assembly as in claim 2 wherein said closure means is removably positioned into and out of said closed position and said closure means being repeatedly recloseable.

4. An assembly as in claim 3 wherein said wiper element is replaceable within said hollow interior and said closure means is positionable into said closed position once therein, whereby said wiper element is storable within said hollow interior of said package means for disposal with said diaper structure.

5. An assembly as in claim 1 wherein said wiper element is of sufficient dimension and structure to clean waste material from the infant after the depositing thereof by the infant into the diaper.

6. An assembly as in claim 1 wherein said package means is formed from a substantially transparent material, said wiper element being viewable through said package.

7. An assembly as in claim 1 wherein said package means is removably mounted on said diaper structure in accessible relation to an adult applying or removing the diaper structure on the infant.

8. An assembly as in claim 7 wherein said package means is mountable on an exterior surface of said diaper structure.

9. An assembly as in claim 1 wherein said closure means is structured to be resistant to opening by an infant.

10. In combination, a disposable diaper structure and a cleaning assembly for use in wiping and cleaning waste material from the skin of an infant deposited thereon when disposal of the waste material is made by the infant in the diaper, said combination comprising:

a. the diaper structure being of the disposable type and removably securable about the waist, buttocks and genitalia of an infant, b. a wiper element formed of a liquid absorbent material and having sufficient softness and texture to be applied to the skin of an infant in the removal of waste therefrom, c. a cleaning composition applied to said wiper element and carried thereby and being of sufficient quantity to moisten said wiper element, d. a package means secured to and outer, exposed surface of said diaper structure and having a hollow interior portion for the containment of the wiper element therein, e. said package means having an opening formed therein and being disposed in communicating relation between said hollow interior portion and the exterior of said package means and being of sufficient dimension to allow passage therethrough of said wiper element, f. closure means mounted on said package means contiguous said opening and structured and disposed in covering, closing relation to said opening for the protection and maintenance of said wiper element within said hollow interior portion and the resistance of said cleaning composition in a non-evaporated state, g. said package means formed of a material resistant to the passage of liquid therethrough and thereby resistant to the evaporation of said cleaning composition from said wiper element and from within said hollow interior portion when said closure means is in said closed position, h. whereby said wiper element is readily available from cleaning of an infant upon removal of the diaper structure therefrom, and i. said closure means comprising a tear strip integrally formed on said package means in covering, closing relation to said opening, said tear strip secured to the remainder of said package by a weakened segment line extending along the length of said tear strip and serving to removably interconnect said tear strip to the remainder of said package means.

11. The combination of claim 10 wherein said package means if fixedly secured to an outer surface of the diaper structure.

* * * * *